(12) United States Patent
Johnson

(10) Patent No.: US 12,285,321 B1
(45) Date of Patent: Apr. 29, 2025

(54) VAGINAL SHIELD

(71) Applicant: Diann Johnson, Round Lake, IL (US)

(72) Inventor: Diann Johnson, Round Lake, IL (US)

( * ) Notice: Subject to any disclaimer, the term of this patent is extended or adjusted under 35 U.S.C. 154(b) by 368 days.

(21) Appl. No.: 17/844,952

(22) Filed: Jun. 21, 2022

(51) Int. Cl.
*A61F 13/472* (2006.01)
*A61B 46/20* (2016.01)
*A61F 13/494* (2006.01)
*A61F 13/511* (2006.01)
*A61F 13/514* (2006.01)

(52) U.S. Cl.
CPC .. *A61F 13/47236* (2013.01); *A61F 13/49413* (2013.01); *A61F 13/51401* (2013.01); *A61B 2046/205* (2016.02); *A61F 2013/51147* (2013.01)

(58) Field of Classification Search
CPC .......... A61F 13/47236; A61F 13/49413; A61F 13/51401; A61F 13/47; A61F 13/472; A61F 2013/51147; A61F 2013/47281; A61F 2013/4562; A61F 2013/4706; A61F 2013/4708; A61B 2046/205
See application file for complete search history.

(56) References Cited

U.S. PATENT DOCUMENTS

| 4,520,807 | A | 6/1985 | Rotter | |
| 4,808,178 | A | 2/1989 | Aziz et al. | |
| 2014/0066875 | A1* | 3/2014 | Hopkins | A61F 13/51394 604/385.01 |
| 2021/0386596 | A1* | 12/2021 | Dennis | A61F 13/55185 |
| 2023/0018845 | A1* | 1/2023 | Lee | A61F 13/4752 |

* cited by examiner

*Primary Examiner* — Ariana Zimbouski
*Assistant Examiner* — Timothy L Flynn
(74) *Attorney, Agent, or Firm* — Sanchelima & Associates, P.A.; Jesus Sanchelima; Christian Sanchelima

(57) ABSTRACT

A vaginal shield including a covering assembly and an absorbing assembly. The covering assembly includes a covering. The covering is made of silicon or gel. The covering is used to cover female genitalia when defecating. The covering can be attached to the female genitalia. The absorbing assembly includes an absorbing pad. The absorbing pad is removably attached to the covering. The absorbing pad is used to absorb fences, blood, or urine. The absorbing pad can be used attached to underwear. The covering can be used attached to female genitalia.

2 Claims, 1 Drawing Sheet

VAGINAL SHIELD

II. BACKGROUND OF THE INVENTION

1. Field of the Invention

The present invention relates to a vaginal shield and, more particularly, to a vaginal shield that covers and protects the female genitalia from receiving feces.

2. Description of the Related Art

Several designs for a vaginal shield have been designed in the past. None of them, however, include an attachable contour to be attached to female genitalia.

Applicant believes that a related reference corresponds to U.S. Pat. No. 4,520,807 issued for an apparatus for minimizing and most likely eliminating contamination during an obstetrical delivery and repair. Applicant believes that another related reference corresponds to U.S. Pat. No. 4,808,178 issued for a disposable absorbent article having elasticized flaps provided with leakage resistant flaps. None of these references, however, teach of a personal protection device comprising a vaginal shield composed of an absorbent pad having a central silicon or gel area, where the device prevents fecal contamination the wearer's vaginal area.

Other documents describing the closest subject matter provide for a number of more or less complicated features that fail to solve the problem in an efficient and economical way. None of these patents suggest the novel features of the present invention.

III. SUMMARY OF THE INVENTION

It is one of the objects of the present invention to provide a vaginal shield that includes gel or silicone to be attached to a female genitalia.

It is another object of this invention to provide a vaginal shield that includes an absorbent pad to absorb urine or feces.

It is still another object of the present invention to provide a vaginal shield that has an oval shape to conform with the shape of the contour of a vagina.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

IV. BRIEF DESCRIPTION OF THE DRAWINGS

Figure 1:
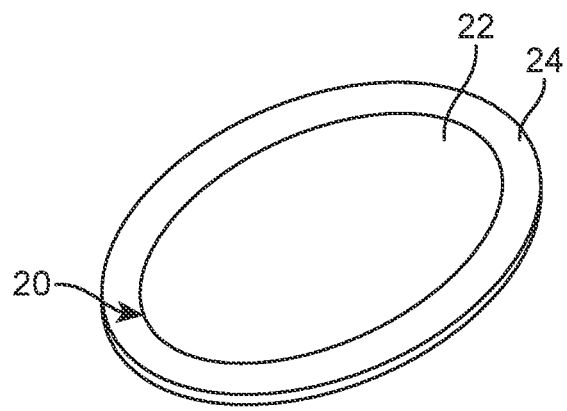

With the above and other related objects in view, the invention consists in the details of construction and combination of parts as will be more fully understood from the following description, when read in conjunction with the accompanying drawings in which:

FIG. 1 represents an isometric view of one embodiment of the present invention 10 including a covering assembly 20.

Figure 2:
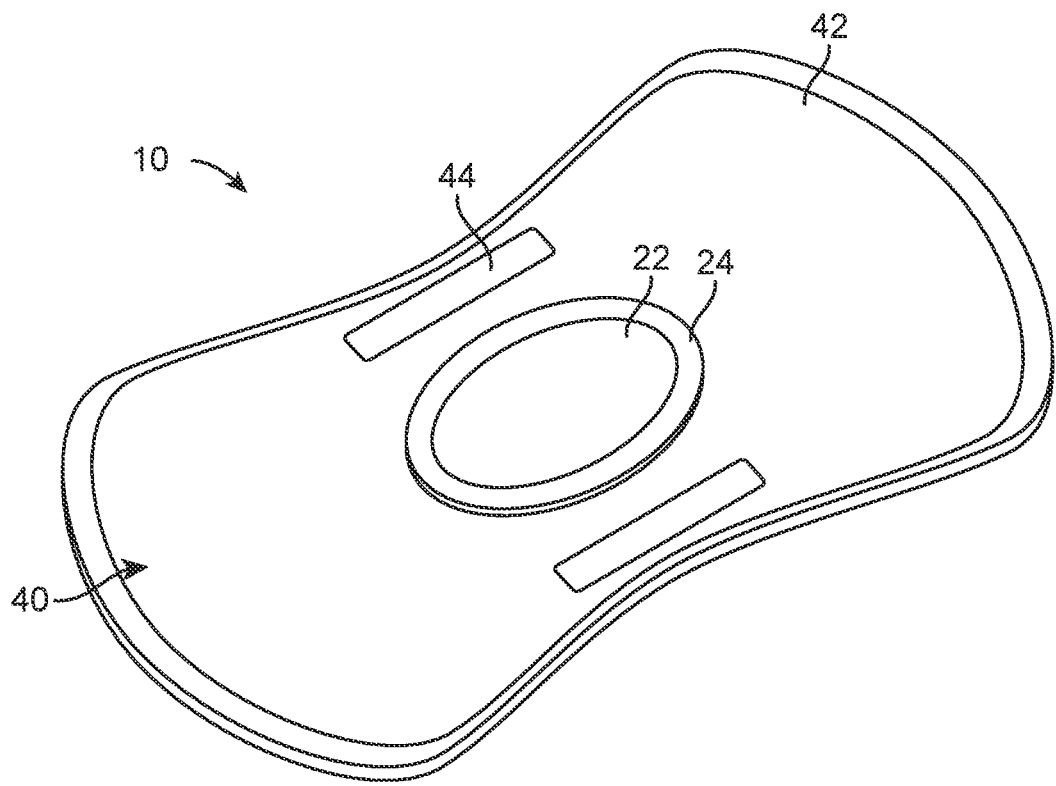

FIG. 2 shows an isometric view of the present invention 10 including a covering assembly 20 and an absorbing assembly 40.

V. DETAILED DESCRIPTION OF THE EMBODIMENTS OF THE INVENTION

Referring now to the drawings, where the present invention is generally referred to with numeral 10, it can be observed that it basically includes a covering assembly 20 and an absorbing assembly 40. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The covering assembly 20 may include an inner portion 22 and an outer portion 24. The inner portion 22 may be made of silicone. It also may be suitable for the inner portion 22 to be made of Polyvinyl Chloride, Polypropylene, rubber, or any other suitable material. In a preferred embodiment the inner portion 22 has an oval shape. It also may be suitable for the inner portion 22 to have a rectangular shape, a circular shape, or any other suitable shape. The inner portion 22 may have a concave depth defining a reservoir. The inner portion 22 of the covering assembly may include protecting gel or fragrance. The inner portion 22 may be attached to the outer portion 24.

The outer portion 24 may have an oval shape. It also may be suitable for the outer portion 24 to have a rectangular shape, a circular shape, or any other suitable shape. The outer portion 24 may be made of silicone. It also may be suitable for the outer portion 24 to be made of Polyvinyl Chloride, Polypropylene, rubber, or any other suitable material. The outer portion 24 may be planar. In a preferred embodiment the outer portion 24 may include a gel or an adhesive to adhere the covering assembly to the surrounding edges of a vagina. In a preferred embodiment the adhesive may be an easy to adhere and remove adhesive. It also may be suitable to add the covering assembly 20 over an inner portion of underwear to be used as a menstruation pad. The inner portion 22 and the outer portion 24 may be attached together defining a concave element that can be attached to a vaginal area of a user. In a preferred embodiment the user may secure the covering assembly 20 surrounding the vagina and clean from the anus to the vagina of the user without contaminating the vagina. The covering assembly 20 may also be used to protect the user from getting any vaginal infection.

The covering assembly 20 may be attached to the absorbing assembly 40. The absorbing assembly 40 may include an absorbing pad 42. The covering assembly 20 may be located on a central portion of the absorbing pad 42. It also may be suitable for the absorbing pad 42 to have any other configuration in the absorbing pad. In a preferred embodiment the absorbing pad 42 may be made of bleached rayon, cotton, and plastics. It also may be suitable for the absorbing pad to be made of any other suitable material to be worn over the underwear. The absorbing pad 42 may have a substantially rectangle shape with rounded ends. It also may be suitable for the absorbing pad 42 to have a circular shape, a triangular shape, or any other suitable shape. The absorbing pad 42 may be ergonomic. The absorbing pad 42 may include fragrances. The absorbing pad 42 may have a polymer inside which can absorb liquid. The present invention 10 may protect the user's vaginal area through the covering assembly 20 for infections and may absorb blood during menstruation or urine.

In a preferred embodiment the absorbing pad 42 may be placed over an inner portion of the underwear. It also may be suitable to secure the absorbing pad 42 to a vaginal area through attaching elements 44. In a preferred embodiment the attaching elements 44 may contain adhesive. The adhesive may be a non-aggressive material for the skin. The attaching elements 44 may have a rectangular shape. It also may be suitable for the attaching elements 44 to have a circular shape, a triangular shape, or any other suitable shape. In a preferred embodiment the attaching elements 44 may be located in a central portion of the absorbing pad 42 on the sides of the covering assembly 20. It also may be suitable for the attaching elements 44 to have any other configuration in the absorbing pad 42. It also may be suitable for the attaching elements 44 to include wings to be attached to the underwear or surrounding a vaginal area. It should be understood that the covering assembly 20 may be used along with the absorbing assembly 40 or separated from the absorbing assembly. In a preferred embodiment the user may secure the absorbing assembly 40 surrounding a vaginal area. The absorbing assembly 40 and the covering assembly 20 may protect from spilling blood or getting any infection.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A vaginal shield, comprising: a covering assembly, wherein said covering assembly includes a covering, wherein said covering is made of silicone or gel, said covering has an inner portion and an outer portion, said inner portion has an oval shape with a concave depth, said outer portion has an oval shape, said outer portion includes adhesive, said adhesive is configured to secure said covering assembly surrounding female genitalia, said covering is configured for covering said female genitalia, wherein said inner portion includes a protecting gel and a fragrance; and an absorbing assembly, wherein said absorbing assembly includes an absorbing pad and attaching elements, wherein the absorbing pad has a rectangular shape with rounded ends, wherein the absorbing pad has a width and a length larger than said covering assembly, wherein the covering assembly is removably attached to a central portion of the absorbing pad, said attaching elements have a rectangular shape, said attaching elements are located in a central portion of the absorbing pad, said attaching elements are configured to secure said absorbing pad to surround said female genitalia, wherein said absorbing pad and said covering have fragrance, said absorbing pad has a polymer inside, said polymer is configured to absorb liquid wherein said absorbing pad is configured to absorb urine or feces.

2. A vaginal shield, consisting of: a covering assembly, wherein said covering assembly includes a covering, wherein said covering is made of silicone or gel, said covering has an inner portion and an outer portion, said inner portion has an oval shape with a concave depth, said outer portion has an oval shape, said outer portion includes adhesive, said adhesive is configured to secure said covering assembly surrounding female genitalia, said covering is configured for covering said female genitalia wherein said inner portion includes a protecting gel and a fragrance; and an absorbing assembly, wherein said absorbing assembly includes an absorbing pad and attaching elements, wherein the absorbing pad has a rectangular shape with rounded ends, wherein the absorbing pad has a width and a length larger than said covering assembly, wherein the covering assembly is removably attached to a central portion of the absorbing pad, said-absorbing pad is removably attached to said covering, said attaching elements have a rectangular shape, said attaching elements are located in a central portion of the absorbing pad, said attaching elements are configured to secure said absorbing pad to surround said female genitalia, wherein said absorbing pad and said covering have fragrance, said absorbing pad has a polymer inside, said polymer is configured to absorb liquid, wherein said absorbing pad is configured to absorb urine or feces.

* * * * *